(12) United States Patent
Gorman

(10) Patent No.: US 7,736,632 B2
(45) Date of Patent: Jun. 15, 2010

(54) TOPICAL DEODORANT COMPOSITION, AND METHOD OF ITS MANUFACTURE AND USE

(76) Inventor: Cynthia DeLaney Gorman, 19737 Bryant St., Winnetka, CA (US) 91306

( * ) Notice: Subject to any disclaimer, the term of this patent is extended or adjusted under 35 U.S.C. 154(b) by 305 days.

(21) Appl. No.: 12/034,221

(22) Filed: Feb. 20, 2008

(65) Prior Publication Data

US 2009/0208438 A1      Aug. 20, 2009

(51) Int. Cl.
*A61K 8/97* (2006.01)
(52) U.S. Cl. .................. 424/65; 424/401; 514/937
(58) Field of Classification Search .................. None
See application file for complete search history.

(56) References Cited

U.S. PATENT DOCUMENTS

| | | | |
|---|---|---|---|
| 4,534,962 A | 8/1985 | Marschner | |
| 5,098,694 A | 3/1992 | Komp et al. | |
| 5,302,381 A | 4/1994 | Greczyn et al. | |
| 6,139,825 A | 10/2000 | Reinhard et al. | |
| 6,193,987 B1 | 2/2001 | Harbeck | |
| 6,558,681 B1 | 5/2003 | Ambrosen et al. | |
| 6,719,966 B2 | 4/2004 | Abrutyn | |
| 6,899,897 B2 | 5/2005 | Battaglia | |
| 7,011,822 B2 | 3/2006 | Guenin et al. | |
| 7,205,012 B1 | 4/2007 | Hill | |
| 7,262,224 B2 | 8/2007 | Chong | |
| 7,288,265 B1 | 10/2007 | Rolf | |
| 2003/0206973 A1 | 11/2003 | Gale | |
| 2003/0228384 A1 | 12/2003 | Kurk et al. | |
| 2004/0247542 A1 | 12/2004 | Horino | |
| 2006/0018867 A1 | 1/2006 | Kawasaki et al. | |
| 2007/0196295 A1 | 8/2007 | Cantwell et al. | |
| 2007/0251840 A1 | 11/2007 | Francis | |
| 2009/0068255 A1* | 3/2009 | Yu et al. ................ 424/450 |

* cited by examiner

*Primary Examiner*—Johann R Richter
*Assistant Examiner*—Hong Yu
(74) *Attorney, Agent, or Firm*—Williamson Intellectual Property Law, LLC; Thomas R. Williamson, III

(57) ABSTRACT

A topical deodorant composition comprising unrefined Shea butter, sodium bicarbonate, cornstarch, cocoa butter, coconut oil, lavender oil, Clary sage oil, benzoin gum tincture and vitamin E. The topical deodorant composition controls body odor and improves the moisture, texture and appearance of the skin. To prepare the topical deodorant composition, unrefined Shea butter, cocoa butter, coconut oil and vitamin E are mixed over hot water at 100° F.-120° F. Cornstarch and sodium bicarbonate are added over hot water at 100° F.-120° F. Subsequently, lavender oil, Clary sage oil and benzoin gum tincture are added. The mixture is removed from heat, cooled to 75° F. and distributed via a glass jar, solid stick or squeezable tube.

20 Claims, No Drawings

TOPICAL DEODORANT COMPOSITION, AND METHOD OF ITS MANUFACTURE AND USE

CROSS-REFERENCE TO RELATED APPLICATIONS

None

FEDERALLY SPONSORED RESEARCH OR DEVELOPMENT

None

PARTIES TO A JOINT RESEARCH AGREEMENT

None

REFERENCE TO A SEQUENCE LISTING

None

BACKGROUND OF THE INVENTION

1. Technical Field of the Invention

The present invention relates generally to a topical deodorant composition, method of its manufacture, and method of use thereof, wherein the topical deodorant composition effectively controls body odor and minimizes skin irritation. The topical deodorant composition comprises a precise mixture of highly effective agents including: unrefined Shea butter, sodium bicarbonate, cornstarch, cocoa butter, coconut oil, lavender oil, Clary sage oil, benzoin gum tincture and vitamin E.

2. Description of Related Art

Body odor is most commonly caused by fatty acids on skin and from malodors from bacteria sources. The unpleasant orders are mainly organic molecules which have different structures and functional groups, such as amines, acids, alcohols, aldehydes, ketones, phenolics, polycyclics, indoles, aromatics, polyaromatics, etc.

Odor modification, in which odor is changed via chemical modification, is known in the art, the most common of which include sodium bicarbonate to reduce malodor. However, many cosmetics and deodorants often have too much sodium bicarbonate, which makes the deodorant break apart very easily and become dry. On the other hand, many deodorants do not have enough sodium bicarbonate, making the deodorant too smooth and thereby less effective at deodorizing.

Additionally, numerous attempts have been made to conceal body odors through use of perfumes. Not only are such perfumes often inadequate at fully concealing body odors, very often they are irritating to the user's skin. The perfume odor itself may be irritating or offensive to the user's respiratory system and/or olfactory senses, as well as to nearby individuals. Additionally, addition of certain scents to a deodorant may actually reduce odor effectiveness. For example, many cosmetics and deodorants add "lavender 40/42," which is a blend of lavender oils that dilute the amount of linalol present in the oil. Adding lavender 40/42 results in a strong scent in a deodorant, but it is not as effective at eliminating body odor as "pure lavender," which is oil that is not diluted with other substances.

Additionally, many deodorants and cosmetics utilize a variety of oil extracts, which are well known in the art to have certain healing and muscle relaxing properties. For example, a massage emollient teaches melting Shea butter in combination with other oils. Additionally, a cosmetic for ultraviolet protection teaches combining Shea butter, sage extract, benzoin gum and coconut oil. However, most of these products do not contain Clary sage oil, and further are not products that both deodorize and provide therapeutic value.

Therefore, it is readily apparent that there is a need for a topical deodorant composition that is not too dry, easy to apply to the skin, effectively fights odor and combines the appropriate quantities of oil extracts.

BRIEF SUMMARY OF THE INVENTION

Briefly described, the present invention is a composition comprising a unique combination of ingredients including unrefined Shea butter, sodium bicarbonate, cornstarch, cocoa butter, coconut oil, lavender oil, Clary sage oil, benzoin gum tincture and vitamin E, and a method of using these ingredients to improve the moisture, texture and appearance of the skin. Additionally, the formulations of the present invention have the unique ability to prevent body odor and irritation to the skin. The compositions can be topically administered via a container, such as, for exemplary purposes only, a glass jar, a rigid tube or a squeezable tube.

According to its major aspects and broadly stated, the present invention in its preferred form is a topical deodorant composition comprising unrefined Shea butter, sodium bicarbonate, cornstarch, cocoa butter, Clary sage oil, benzoin gum tincture, coconut oil, lavender oil, vitamin E and other optional oil extracts.

Generally, the topical deodorant composition comprises from about 56.7% to about 61.7% by weight of unrefined Shea butter, from about 15.3% to about 21.0% by weight of sodium bicarbonate, from about 10.1% to about 14.0% by weight of cornstarch, from about 0.9% to about 13.5% by weight of cocoa butter, from about 1.1% to about 1.3% by weight of Clary sage oil, from about 0.3% to about 0.6% by weight of benzoin gum tincture, from about 0.9% to about 1.1% by weight of coconut oil, from about 1.2% to about 1.4% by weight of lavender oil and about 0.2% by weight of vitamin E.

In particular, if the topical deodorant composition is dispensed from a glass jar, the topical deodorant composition comprises approximately: 58.9% by weight of unrefined Shea butter, 21.0% by weight of sodium bicarbonate, 14.0% by weight of cornstarch, 2.0% by weight of cocoa butter, 1.2% by weight of Clary sage oil, 0.6% by weight of benzoin gum tincture, 1.0% by weight of coconut oil, 1.2% by weight of lavender oil and 0.2% by weight of vitamin E.

If the topical deodorant composition is dispensed as a solid stick, the topical deodorant composition comprises approximately: 56.7% by weight of unrefined Shea butter, 15.3% by weight of sodium bicarbonate, 10.1% by weight of cornstarch, 13.5% by weight of cocoa butter, 1.3% by weight of Clary sage oil, 0.3% by weight of benzoin gum tincture, 1.1% by weight of coconut oil, 1.4% by weight of lavender oil and 0.2% by weight of vitamin E.

Lastly, if the topical deodorant composition is dispensed from a squeezable tube, the topical deodorant composition comprises approximately: 61.7% by weight of unrefined Shea butter, 20.0% by weight of sodium bicarbonate, 13.4% by weight of cornstarch, 0.9% by weight of cocoa butter, 1.1% by weight of Clary sage oil, 0.5% by weight of benzoin gum tincture, 0.9% by weight of coconut oil, 1.2% by weight of lavender oil and 0.2% by weight of vitamin E.

To manufacture the topical deodorant composition, unrefined Shea butter, cocoa butter, coconut oil and vitamin E are mixed together over hot water, wherein the hot water is maintained at 100° F.-120° F. The mixture is then stirred until completely melted. Cornstarch and sodium bicarbonate are then added to the mixture over hot water, wherein the hot water is also maintained at 100° F.-120° F. until the sodium bicarbonate dissolves completely. The mixture is then removed from heat and cooled to 75° F. Subsequently, lavender oil, Clary sage oil and benzoin gum tincture are added to the mixture. After the mixture has cooled it is then packaged into a glass jar, squeezable tube or stick container, depending on composition, whereby a user directly applies the topical deodorant composition to his or her skin.

More specifically, the present invention is an effective topical deodorant composition comprising the following ingredients: unrefined Shea butter, sodium bicarbonate, cornstarch, cocoa butter, coconut oil, lavender oil, Clary sage oil, benzoin gum tincture and vitamin E. The combination of these ingredients provides a synergistic result, wherein it was discovered that the addition of Clary sage oil, in addition with other ingredients, effectively controls body odor, while other sage oil compositions were found to be not effective. Further, it was found that by the use of Clary sage oil, the quantity of sodium bicarbonate could be reduced, thereby reducing the dryness of the composition, while providing improved deodorizing qualities.

Additionally, the applicant has discovered the precise order of mixing each ingredient in the composition to maximize odor protection and therapeutic qualities. First, unrefined Shea butter, cocoa butter, coconut oil and vitamin E are melted over heat and mixed together. Second, cornstarch and sodium bicarbonate are added over heat until all the sodium bicarbonate dissolves, wherein the sodium bicarbonate is precisely measured to ensure the composition is not too dry and not too smooth. Lastly, the heat is removed and lavender oil, Clary sage oil and benzoin gum tincture are added. The composition is subsequently cooled and stored into a glass jar, solid stick or squeezable tube. Following this method of manufacture maximizes the composition's deodorant and therapeutic qualities.

Accordingly, one feature and advantage of the present invention is its ability to keep the underarms fresh and deodorized without harsh chemicals and/or petroleum by-products.

Another feature and advantage of the present invention is that it is gentle and delicate to the skin and environment.

Yet another feature and advantage of the present invention is its ability to provide long lasting and effective odor protection.

Another feature and advantage of the present invention is its ability to provide a natural subtle scent that does not interfere with perfume or cologne.

Yet another feature and advantage of the present invention is its ability to deodorize skin via a creamy mixture that is not too dry.

Another feature and advantage of the present invention is its ability to provide therapeutic value.

Another feature and advantage of the present invention is its ability to go on clear with no white residue.

These and other features and advantages of the present invention will become more apparent to one skilled in the art from the following description and claims.

DETAILED DESCRIPTION OF THE PREFERRED AND SELECTED ALTERNATE EMBODIMENTS

In describing the preferred and selected alternate embodiments of the present invention, specific terminology is employed for the sake of clarity. The invention, however, is not intended to be limited to the specific terminology so selected, and it is to be understood that each specific element includes all technical equivalents that operate in a similar manner to accomplish similar functions.

A topical deodorant should possess all of the following desirable properties: long lasting and effective reduction of body odor, gentle to the skin and environment, no irritation to the skin from harsh chemicals and/or petroleum by-products, a long shelf life and a therapeutic and pleasant scent that does not interfere with perfume or cologne.

The present invention is based on the unexpected discovery that unique combinations of the following ingredients, described more fully in Table 1, meet all of the above-cited criteria, and in particular the addition of Clary sage oil provides a synergistic result, allowing a reduction of sodium bicarbonate. Sage oil is commonly known in the art as therapeutic oil; however, it is not recognized as an ingredient with deodorizing capabilities. However, after numerous tests, applicant has discovered that introduction of Clary sage oil in a precise amount and in combination with other ingredients forms a unique composition that effectively provides odor protection.

Additionally, in the course of extensive experimentation, it was discovered that the precise order of mixing each ingredient in the composition must be followed to maximize odor protection and therapeutic qualities. In particular, the precise amount of sodium bicarbonate must be controlled to ensure the composition is not too dry or too smooth. Further, it was identified that sodium bicarbonate and cornstarch must be completely dissolved to effectively maximize odor protection.

In the following Table I, the various ingredients are identified, along with their characteristics:

TABLE 1

Ingredients for Use in Formulations of the Present Invention

| Ingredient Name: | Characteristics: |
| --- | --- |
| Unrefined Shea butter (*Butyrospermum parkii*) | Shea butter is an emollient. Specifically, Shea butter is slightly ivory granulate butter consisting of mostly triglycerides, including a fair amount of linoleic acid, and unsaponifiables. |
| Sodium bicarbonate | Sodium bicarbonate is known in the art for its use as an odor absorber. |
| Cornstarch (Amylose) | Cornstarch is a high molecular weight polymer composed of repeating 1,4-alpha-D-glucopyranosyl units and is typically a mixture of linear component, amylase, and a branched component, amylopetic. |
| Cocoa butter (*Theobrama cacao*) | Cocoa butter is commonly known in the art and generally refers to the fat from cocoa beans used to prepare chocolate. Cocoa beans are obtainable from the pods of cacao tree. |
| Coconut oil (*Cocos nucifera*) | Coconut oil is commonly known in the art and generally refers to the concentrate of the coconut milk of *Cocos nucifera*. The coconut milk concentrate is a pale yellow liquid which is soluble in water and alcohol. |
| Lavender oil (*Lavendula angustifolia*) | Lavender oil is obtained by steam distillation from flowers of |

TABLE 1-continued

Ingredients for Use in Formulations of the Present Invention

| Ingredient Name: | Characteristics: |
|---|---|
|  | *Lavendula angustifolia*. Lavender oil comprises linalol, linaylyl acetate lavandulol, lavendaulyl acetate, 3-octanol, α-pinene, β-pinene, limonene, cineole, and citronellal. |
| Clary sage oil (*Salvia sclarea*) | Clary sage oil is obtained by steam distillation from whole plants or flowers of *Salcia sclarea* L. The oil comprises, for example, l-linalol, linalyl acetate, scrareol, and neroridol. |
| Benzoin gum tincture (*Styrax benzoin*) | The tincture of benzoin component, a balsamic gum solution, is included for it highly effective skin-protective and antiseptic properties. However, since this chemical component can cause allegoric skin reactions in some cases, its use is limited to relatively small amounts. |
| Vitamin E | Vitamin E is a fat-soluble vitamin that exists in eight different forms. Each form has its own biological activity, which is measured of potency or functional use in the body. |

Depending upon application, the topical deodorant composition of the present invention comprises the following ratios of components, namely, between approximately 35.0 and approximately 66.0 grams of Shea butter, between approximately 21.4 and approximately 27.0 grams of sodium bicarbonate, between approximately 14.3 and approximately 18.0 grams of cornstarch, between approximately 1.0 and approximately 45.0 grams of cocoa butter, approximately 28.6 to 35.0 drops of and Clary sage oil, between approximately 8.6 and approximately 10.0 drops of benzoin gum tincture, approximately 1.0 grams of coconut oil, and approximately 28.6 to 35.0 drops of lavender oil. Further, the composition may include approximately 1.0 to 3.7 drops of vitamin E.

EXAMPLES

The following non-limiting examples illustrate the formulations of the present composition.

Example I

The following example illustrates the composition and preparation of same for application via a glass jar:

| INGREDIENT | WEIGHT |
|---|---|
| Unrefined Shea butter | 420 grams |
| Sodium bicarbonate | 150 grams |
| Cornstarch | 100 grams |
| Cocoa butter | 14 grams |
| Coconut oil | 7 grams |
| Lavender oil | 200 drops |
| Clary sage oil | 200 drops |
| Benzoin gum tincture | 60 drops |
| Vitamin E | 26 drops |

The approximate weight of the above composition of ingredients is as follows and is subsequently utilized for calculating percentages:

| INGREDIENT | APPROXIMATE WEIGHT (GRAMS) |
|---|---|
| Unrefined Shea butter | 420 grams |
| Sodium bicarbonate | 150 grams |
| Cornstarch | 100 grams |
| Cocoa butter | 14 grams |
| Coconut oil | 7 grams |
| Lavender oil | 8.85 grams |
| Clary sage oil | 8.29 grams |
| Benzoin gum tincture | 3.93 grams |
| Vitamin E | 1.24 grams |

Prepare the composition of Example I by the following steps: create a mixture by mixing unrefined Shea butter, cocoa butter, coconut oil and, optionally, vitamin E together over hot water at approximately 100° F. to 120° F. Stir the mixture until the mixture is melted. Subsequently, cornstarch and sodium bicarbonate are added and the mixture is continually stirred over hot water approximately 100° F. to 120° F. until the cornstarch and sodium bicarbonate are completely dissolved. Remove heat and add lavender oil, Clary sage oil and benzoin gum tincture into the mixture. Allow the mixture to cool to 75° F., wherein the mixture thickens to form a soft creamy base.

Prepare the mixture for application to the skin by positioning the resulting composition into a glass jar for containment and storage.

Example II

The following example illustrates the composition and preparation of same for application via a solid stick:

| INGREDIENT | WEIGHT |
|---|---|
| Unrefined Shea butter | 245 grams |
| Sodium bicarbonate | 189 grams |
| Cornstarch | 126 grams |
| Cocoa butter | 315 grams |
| Coconut oil | 7 grams |
| Lavender oil | 245 drops |
| Clary sage oil | 245 drops |
| Benzoin gum tincture | 70 drops |
| Vitamin E | 7 drops |

The approximate weight of the above composition of ingredients is as follows and is subsequently utilized for calculating percentages:

| INGREDIENT | APPROXIMATE WEIGHT (GRAMS) |
|---|---|
| Unrefined Shea butter | 245 grams |
| Sodium bicarbonate | 189 grams |
| Cornstarch | 126 grams |
| Cocoa butter | 315 grams |
| Coconut oil | 7 grams |
| Lavender oil | 10.84 grams |
| Clary sage oil | 10.93 grams |
| Benzoin gum tincture | 4.59 grams |
| Vitamin E | 0.33 grams |

To prepare the composition of Example II, mix unrefined Shea butter, cocoa butter, coconut oil and, optionally, vitamin E over hot water at 100° F.-120° F. Stir the mixture until the ingredients are completely melted. Add cornstarch and sodium bicarbonate over hot water, wherein the hot water is also maintained at 100° F.-120° F., stirring until the sodium bicarbonate is completely dissolved. Subsequently, lavender oil, Clary sage oil and benzoin gum tincture are added to the mixture. The mixture is then removed from heat and cooled to 75° F.

Prepare the mixture for application to the skin by loading the resulting composition into a solid stick deodorant, wherein the composition is utilized via, for exemplary purposes only, a twist and push-up applicator.

Example III

The following example illustrates the composition and preparation of same for application via a squeezable tube:

| INGREDIENT | WEIGHT |
| --- | --- |
| Unrefined Shea butter | 462 grams |
| Sodium bicarbonate | 150 grams |
| Cornstarch | 100 grams |
| Cocoa butter | 7 grams |
| Coconut oil | 7 grams |
| Lavender oil | 200 drops |
| Clary sage oil | 200 drops |
| Benzoin gum tincture | 60 drops |
| Vitamin E | 26 drops |

The approximate weight of the above composition of ingredients is as follows and is subsequently utilized for calculating percentages:

| INGREDIENT | APPROXIMATE WEIGHT (GRAMS) |
| --- | --- |
| Unrefined Shea butter | 462 grams |
| Sodium bicarbonate | 150 grams |
| Cornstarch | 100 grams |
| Cocoa butter | 7 grams |
| Coconut oil | 7 grams |
| Lavender oil | 8.85 grams |
| Clary sage oil | 8.29 grams |
| Benzoin gum tincture | 3.93 grams |
| Vitamin E | 1.24 grams |

Prepare the composition of Example III by the following steps: add unrefined Shea butter, cocoa butter, coconut oil and, optionally, vitamin E over hot water at approximately 100° F. to 120° F. Stir the mixture until it is melted. Subsequently, add cornstarch and sodium bicarbonate and continue to stir the mixture over hot water at approximately 100° F. to 120° F. until the cornstarch and sodium bicarbonate are completely dissolved. Remove heat and add lavender oil, Clary sage oil and benzoin gum tincture. Allow the mixture to cool to 75° F.

Prepare the mixture for application to the skin by positioning the resulting composition into a squeezable tube.

The proceeding examples can be repeated with similar success by substituting the generically specifically-described reactants for those utilized in the proceeding examples.

In an alternate embodiment of the present invention, it has been found that the composition could be made with the following ratio of components, wherein Shea butter could be varied between 245 and 462 grams, baking soda could be utilized between 25 and 225 grams, cornstarch could be varied between 25 and 225 grams, cocoa butter could range from 7 to 315 grams, coconut oil could range between 3.5 and 14 grams, lavender oil and Clary sage oil could be varied between 100 and 300 drops, benzoin gum tincture could be utilized between 20 and 120 drops, and vitamin E could range between 0 and 80 drops, while still retaining the deodorizing and healing characteristics of the preferred embodiments.

The foregoing description comprises illustrative preferred and alternative embodiments of the present invention. Having thus described exemplary embodiments of the present invention, it should be noted by those skilled in the art that the within disclosures are exemplary only, and that various other alternatives, adaptation, and modifications may be made within the scope of the present invention. Merely listing the steps of the method in a certain order does not necessarily constitute any limitation on the order of the steps of the method. Many modifications and other embodiments of the invention will come to mind to one skilled in the art to which this invention pertains having the benefit of the teachings presented in the foregoing descriptions. Therefore, it is to be understood that the invention is not to be limited to the specific embodiments disclosed and that modifications and other embodiments are intended to be included within the scope of the claims. Although specific terms are employed herein, they are used in a generic and descriptive sense only and not for purposes of limitation. Accordingly, the present invention is not limited to the specific embodiments illustrated herein, but is limited only by the following claims.

What is claimed is:

1. A topical deodorant composition comprising:
   unrefined Shea butter;
   sodium bicarbonate;
   cornstarch;
   cocoa butter;
   Clary sage oil;
   benzoin gum tincture;
   coconut oil;
   lavender oil; and
   optionally, vitamin E and optional oil extracts.

2. The topical deodorant composition of claim 1, wherein said unrefined Shea butter comprises from about 27.0% to about 61.7% by weight of said topical deodorant composition.

3. The topical deodorant composition of claim 1, wherein said sodium bicarbonate comprises from about 20.0% to about 21.0% by weight of said topical deodorant composition.

4. The topical deodorant composition of claim 1, wherein said cornstarch comprises from about 13.4% to about 14.0% by weight of said topical deodorant composition.

5. The topical deodorant composition of claim 1, wherein said cocoa butter comprises from about 0.9% to about 34.7% by weight of said topical deodorant composition.

6. The topical deodorant composition of claim 1, wherein said Clary sage oil comprises from about 0.01% to about 1.2% by weight of said topical deodorant composition.

7. The topical deodorant composition of claim 1, wherein said benzoin gum tincture comprises from about 0.005% to about 0.6% by weight of said topical deodorant composition.

8. The topical deodorant composition of claim 1, wherein said coconut oil comprises from about 0.008% to about 1.0% by weight of said topical deodorant composition.

9. The topical deodorant composition of claim 1, wherein said lavender oil comprises from about 0.01% to about 1.2% by weight of said topical deodorant composition.

10. The topical deodorant composition of claim 1, wherein said vitamin E comprises from about 0.0004% to about 0.2% by weight of said topical deodorant composition.

11. The topical deodorant composition of claim 1, comprising:
- 58.9% unrefined Shea butter;
- 21.0% sodium bicarbonate;
- 14.0% cornstarch;
- 2.0% cocoa butter;
- 1.2% Clary sage oil;
- 0.6% benzoin gum tincture;
- 1.0% coconut oil;
- 1.2% lavender oil; and
- 0.2% vitamin E.

12. The topical deodorant composition of claim 1, comprising:
- 26.7% unrefined Shea butter;
- 20.8% sodium bicarbonate;
- 13.9% cornstarch;
- 34.67% cocoa butter;
- 0.01% Clary sage oil;
- 0.005% benzoin gum tincture;
- 0.008% coconut oil;
- 0.01% lavender oil; and
- 0.0004% vitamin E.

13. The topical deodorant composition of claim 1, comprising:
- 61.7% unrefined Shea butter;
- 20.0% sodium bicarbonate;
- 13.4% cornstarch;
- 0.9% cocoa butter;
- 1.1% Clary sage oil;
- 0.5% benzoin gum tincture;
- 0.9% coconut oil;
- 1.2% lavender oil; and
- 0.2% vitamin E.

14. The topical deodorant composition of claim 1 comprising the following rations: from about 35.0 to about 66.0 grams of shea butter; from about 21.4 to about 27.0 grams of sodium bicarbonate; from about 14.3 to about 18.0 grams of cornstarch; from about 1.0 to about 45.0 grams of cocoa butter; from about 28.6 to about 35.0 drops of Clary sage oil; from about 8.6 to about 10.0 drops of benzoin gum tincture; about 1.0 grams of coconut oil; and from about 28.6 to about 35.0 drops of lavender oil.

15. The topical deodorant composition of claim 14, further comprising:
approximately 1.0 to 3.7 drops of vitamin E.

16. A method of applying a topical deodorant composition of unrefined Shea butter, sodium bicarbonate, cornstarch, cocoa butter, Clary sage oil; benzoin gum tincture, coconut oil, lavender oil and optionally, vitamin E, said method comprising the step of:
applying said topical deodorant composition to an area of skin.

17. The method of claim 16, further comprising the step of:
positioning said topical deodorant composition in a glass jar.

18. The method of claim 16, further comprising the step of:
loading said topical deodorant composition as a solid stick into a dispenser.

19. The method of claim 16, further comprising the step of:
positioning said topical deodorant composition in a squeezable tube.

20. A process of manufacturing a topical deodorant composition, said process comprising:
mixing unrefined Shea butter, cocoa butter, coconut oil and vitamin E into a mixture;
heating said mixture over hot water at approximately 100° F. to 120° F.;
stirring said mixture until said mixture is melted;
adding cornstarch and sodium bicarbonate into said mixture, wherein said mixture is stirred and heated over hot water at approximately 100° F. to 120° F. until said cornstarch and said sodium bicarbonate are completely dissolved;
removing said mixture from heat;
adding lavender oil, Clary sage oil and benzoin gum tincture into said mixture; and
cooling said mixture to 75° F.;
packaging said mixture into a container, said container being selected from the group consisting of a glass jar, a rigid tube and a squeezable tube.

* * * * *